United States Patent [19]

Fugo

[11] Patent Number: 5,423,815
[45] Date of Patent: Jun. 13, 1995

[54] METHOD OF OCULAR REFRACTIVE SURGERY

[76] Inventor: Richard J. Fugo, 1507 Plymouth Blvd., Norristown, Pa. 19401

[21] Appl. No.: 186,764

[22] Filed: Jan. 25, 1994

[51] Int. Cl.$^6$ ............................................. A61B 17/36
[52] U.S. Cl. ...................................................... 606/50
[58] Field of Search ...................... 606/33, 49, 50, 51, 606/52, 107, 161, 166, 34, 40; 607/99, 98

[56] References Cited

U.S. PATENT DOCUMENTS 4,326,529  4/1982  Doss et al. ...................... 128/303.1

OTHER PUBLICATIONS

Waring, "Refractive Keratotomy for Myopia and Astigmatism," Mosby–Yearbook, Inc., 164–166, 1992.
Thornton, "Astigmatic Keratotomy: A Review of the Basic Concepts with Case Reports," J. Cat. Refract. Surg., vol. 16, 430–435, Jul., 1990.

*Primary Examiner*—Lee S. Cohen
*Assistant Examiner*—Stephen Huang

[57] ABSTRACT

A method of ocular refractive surgery which employs heat application to reshape and enhance the refractive power of the central cornea of a surgical subject. Radio frequency energy is employed to coagulate segments of corneal stroma in the perilimbal area at the pole of the corneal meridian having the lowest keratometric reading, causing the radius of curvature of the central cornea to increase in that meridian, whereby astigmatism can be safely and permanently corrected.

14 Claims, No Drawings

METHOD OF OCULAR REFRACTIVE SURGERY

BACKGROUND—FIELD OF INVENTION

This invention relates to methods of ocular refractive surgery, specifically to surgical methods of reshaping the cornea employing the application of radio frequency energy and heat into the stroma of the cornea.

BACKGROUND—DESCRIPTION OF PRIOR-ART

The application of heat to areas of the stroma layer of the cornea has been employed to reshape the cornea and effect correction of refractive errors of the eye. Generally referred to as thermokeratoplasty, the heat applications effect corneal reshaping by causing coagulation and shrinkage of the collagen fibers in the stroma. Heretofore, use of heat applications to reshape the cornea has been limited by corneal complications including heat related damage to the epithelium, Bowman's membrane, and endothelium, inducement of irregular astigmatism, and regression of the refractive correction obtained.

As described in *Refractive Keratotomy for Mopia and Astigmatism*, by George Waring, III, M.D., pp. 164-166, published by Mosby-Year Book, Inc., 1992, Fyodorov has employed heat application to correct hyperopia and presbyopia. Fyodorov's method employs an apparatus to puncture the cornea in order to apply heat to the stromal tissue. These punctures and heat applications are made radially or peripherally to produce changes in corneal shape and consequent changes in the refractive power of the cornea. However, use of the Fyodorov method requires invasive puncturing of the cornea which may lead to vision threatening infection and may also cause visual disturbances due to scarring and weakening of the cornea. Moreover, the Fyodorov method requires heat application to thinner portions of the clear cornea located centrally in relation to the limbus, presenting an increased risk of both permanent endothelial cell damage and occurrence of induced irregular astigmatism and associated permanent visual distortion. Also, use of the Fyodorov method requires expensive specialized equipment.

Doss, et. al., U.S. Pat. No. 4,326,529, Apr. 27, 1982, describes an apparatus which employs electric current to apply heat to the stroma to effect corneal reshaping. However, the apparatus requires the use of a circulating saline coolant to prevent over-heating of the epithelium and Bowman's membrane layers of the cornea. Moreover, the apparatus requires the passage of electric current through the entire eye and to an electrode fixed to the head of the surgical subject. This passage of current through ocular tissue may have permanently damaging effects on the cornea, retina, and optic nerve. Also, use of the apparatus causes corneal opacities which could persist for up to ten weeks. Furthermore, use of the apparatus does not permit application of heat to a precise point on the surface of the cornea due to the current and heat dissipating effects of the conductive saline coolant and the configuration of the probe tip. Therefore, excessive areas of the cornea may be heated unnecessarily, increasing the risk of heat-related damage to the endothelium and permanent visual distortion caused by induced irregular astigmatism.

Prior-art thermokeratoplastic methods have the following disadvantges:

(a) increased risk of damaging the non-regenerating endothelial layer of the cornea,
(b) scarring and clouding of the clear portion of the cornea,
(c) development of vision-threatening infections and weakening of the cornea due to invasive puncturing of the cornea,
(d) creation of excessive temperature levels in the thinner, non-peripheral areas of the cornea, resulting in induced irregular astigmatism and permanent visual distortion,
(e) passage of electric current through the entire eye, which may have permanently damaging effects on the cornea, retina, and optic nerve,
(f) production of corneal opacities,
(g) regression of the desired refractive error correction achieved,
(h) use of expensive specialized equipment is required.

SUMMARY OF THE INVENTION

My invention is a method of ocular refractive surgery whereby astigmatism is corrected by coagulating the stromal tissue of the perilimbal area of the eye of a surgical subject. Arcuate sections of the perilimbal area are coagulated at or near the poles of the corneal meridian having the lowest keratometric reading-and necessarily-the least refractive power. Coagulation of the stromal tissue in the perilimbal area causes the radius of curvature of the meridian to increase, resulting in a corresponding increase in the refractive power of the central cornea. My method of correcting astigmatism may be performed independent of other surgical procedures or may easily be used in conjunction with surgical procedures which may cause induced astigmatism, such as cataract surgery.

Briefly and basically, in accordance with the present invention, my method of ocular refractive surgery correcting astigmatism includes the steps of coagulating the corneal stroma in the perilimbal area of the eye by heating arcuate sections of the perilimbal area at or near the poles of the corneal meridian having the lowest keratometric reading. The heat, which is produced through the use of radio frequency energy supplied by a generator, causes a reorganization of the stromal tissue and consequent coagulation and shrinkage of stromal collagen fibers, resulting in an increase in the radius of curvature of the central cornea in the meridian chosen. This increase in corneal curvature causes a corresponding increase in the refractive power of the central cornea, correcting the astigmatic condition, improving visual acuity, and reducing or eliminating the surgical subject's need for external corrective lenses.

OBJECTS AND ADVANTAGES

Accordingly, several objects and advantages of the instant invention are:

(a) to provide a surgical method of correcting astigmatism which does not require invasive incisions nor puncture wounds to be made in the cornea,
(b) to provide a method other than employing corrective eyewear to reduce and correct refractive errors caused by astigmatism,
(c) to provide a method for correcting surgically induced astigmatism which can easily be employed in conjunction with the causative surgery, (d) to provide a surgical method of correcting astigmatism by coagulating corneal stroma tissue which does not cause scarring and clouding of the cornea, (e) to provide a surgical method of correcting astigmatism by coagulating corneal stroma tissue in the perilimbal area at or near the limbus whereby the risk of heat-related damage to endothelial cells is minimized, (f) to provide a surgical method of correcting astigmatism whereby corneal stroma tissue is coagulated only in the peripheral limbal areas of the cornea, eliminating the risk of opacities forming in the clear cornea, (g) to provide a surgical method of correcting astigmatism by coagulating corneal stroma tissue which method does not induce vision-imparing irregular astigmatism, (h) to provide a surgical method of correcting astigmatism by coagulating corneal stroma tissue in which the eye is completely healed within a few days of surgery and whereby permanent change in the curvature of the cornea is achieved.

(i) to provide a surgical method of correcting astigmatism by coagulating corneal stroma tissue which does not require the passage of electric current through the entire eye, reducing the risk of damage to the cornea, retina, and optic nerve, (j) to provide a surgical method of correcting astigmatism by coagulating corneal stroma tissue which does not require the use of expensive specialized equipment.

Further objects and advantages of my invention will become apparent from a consideration of the ensuing description.

DETAILED DESCRIPTION OF THE PREFERRED EMBODIMENTS

My method of ocular refractive surgery is different from all surgical techniques employed to correct refractive errors in an astigmatic surgical subject. Radio frequency energy is employed to coagulate arcuate sections of corneal stroma tissue in the perilimbal area, at or immediately adjacent to the limbus. These arcuate sections are created at the poles of the corneal meridian having the lowest keratorefractive reading. Pursuant to the principles of coupling as described in the article *Astigmatic Keratotomy: A Review of the Basic Concepts with Case Reports*, by Spencer p. Thornton, M.D., J. Cataract Refract. Surg., pp. 430–435, vol. 16, July 1990, the coagulated corneal stroma causes an increase in the radius of curvature of the central cornea at a selected meridian, thereby increasing the refractive power of the central cornea and improving the visual acuity of the surgical subject without the use of external corrective lenses.

A generator such as those presently available commercially and known in the art of ocular surgery is employed to produce radiofrequency energy to heat the corneal stroma of the perilimbal area in the eye of an astigmatic surgical subject. In the preferred embodiment, a bipolar forceps such as those typically employed in electrosurgery of the eye is coupled to the radio frequency energy source and a desired power level for coagulation is selected. It is advisable to begin with a lower power setting and adjust the intensity upward as required. However, high power levels for coagulation are not required and should be avoided as the risk of tissue damage is increased.

Prior to surgery, keratometric measurements of the surgical subject's astigmatic cornea are meticulously evaluated and the corneal meridian having the lowest keratometric reading is determined. The generator is activated, supplying radio frequency energy to the bipolar forceps. The bipolar forceps then are manipulated to contact the perilimbal area of the surgical subject's cornea at the limbus or the immediately adjacent clear cornea. The exact demarcation of the limbus is often difficult to determine due to the transitional nature of the ocular tissue in the limbal zone.

The bipolar forceps contact the perilimbal area of the cornea at the poles of the corneal meridian previously determined to have the lowest keratometric reading. The radio frequency energy passing between the tips of the bipolar forceps causes heat to be generated in the underlying corneal stroma of the perilimbal area contacted. The underlying corneal stroma tissue is coagaluted in arcuate segments by contacting with the bipolar forceps the perilimbal tissue at the poles of the meridian selected and the perilimbal area adjacent to the poles. It is preferred that the length of each coagulated arcuate segment of stromal tissue be evenly divided at poles of the meridian selected. The heat generated by the radio frequency energy causes the collagen fibers of the corneal stroma beneath the perilimbal area contacted by the bipolar forceps to coagulate and shrink, thereby increasing the radius of curvature of the corneal meridian selected, resulting in an increase in the refractive power of the central cornea at the meridian selected. Thus the unaided visual acuity of the surgical subject is improved.

The use of the bipolar forceps permits controlled, focused application of heat and radio frequency energy to those segments of perilimbal corneal tissue at and adjacent to the selected corneal meridian poles. The localized nature of the radio frequency energy passing between the tips of the bipolar forceps inhibits current flow through the entire eye and body, greatly reducing the risk of damage due to stray current. Thus, heat application is limited to coagulate and shrink only those segments of corneal stroma necessary to effect the desired degree of corneal reshaping.

The perilimbal tissue is chosen as the area of heat and radio frequency energy application because the epilethialial layer and stroma layer of the cornea is thickest at the limbus. Therefore the underlying endothelial layer is well-insulated and protected from the effects of the radio frequency energy and heat generated by the bipolar forceps, greatly decreasing the risk that the endothelial cells will be damaged. Moreover, because the area of eye tissue coagulated is located at the outermost edge of the cornea, any potential scarring of the cornea will be least likely to cause visual distortions and the risk of induced irregular astigmatism is eliminated.

Keratometric readings must also be meticulously measured intraoperatively to guard against excessive over-correction of the astigmatic condition. Immediately following cataract surgery, care must be taken to inflate the eye to normal pressure levels in order to observe true physiologic changes in corneal topography. The length of the coagulated arcuate segments created range between 1 mm to 6 mm. It has been observed that the radius of corneal curvature increases as the length of the coagulated arcuate segments is increased. Although the coagulation of perilimbal tissue in the manner herein described effects permanent increases in the radius of curvature of the cornea, there may be a degree of regression toward the pre-operative corneal curvature.

By carefully increasing the intensity of the radio frequency energy employed and by increasing the coagulated arcuate segments of the perilimbal corneal tissue, this regression can be lessened. It has been observed that an over-correction by about two diopters of corneal refractive power will counteract the regression. Thus, when the regression is complete, the desired degree of permanent corneal reshaping and refractive correction is attained. Although the desired degree of corneal curvature increase may be attained by coagulating perilimbal stroma at only one pole of the corneal meridian selected, most surgical cases will require heat application at both poles.

The application of heat in the manner described herein will cause coagulation and whitening of epithelial cells in the cornea of the perilimbal area contacted by the bipolar forceps. However, these epithelial cells quickly regenerate such that within only a few days after the procedure is performed, no physiologic changes to the eye are visible by slit slamp examination and the eye is completly healed.

Because the heat application is effected at the thickest region of the cornea, the risk of induced irregular astigmatism is eliminated. Other techniques employing heat to coagulate stromal tissue have an increased risk of induced irregular astigmatism because stromal tissue can be coagulated in the thinner, more centrally located areas of the cornea. Moreover, my method of ocular refractive surgery does not require that the cornea be incised or punctured, greatly reducing the risk of postoperative infection and eliminating the risk of the scarring and weakening of the cornea that can be caused by invasive incisions and puncture wounds.

SUMMARY, RAMIFICATIONS, AND SCOPE

Accordingly, the reader will see that the method of ocular refractive surgery of this invention provides a safe, efficient, economical means for ocular surgeons to correct astimatisms in surgical subjects by the application of heat to the corneal stroma. When the method described above is implemented, permanent correction of refractive error due to astigmatisms can be attained and the ocular tissue of the surgical subject will be completely healed after only a few days post operation. Further, this invention has further advantages in that:

- it does not require invasive incisions nor puncture wounds to be made in the cornea;
- it eliminates or reduces dependence on external corrective lenses to correct refractive errors due to astigmatism;
- it provides an ocular refractive surgical method which can easily be employed in conjunction with other surgical procedures;
- it provides a method of correcting astigmatism by applying heat to the corneal stroma which does not cause scarring and clouding of the cornea;
- it provides a method of heating corneal stroma tissue to correct astigmatism which greatly reduces the risk of heat-related damage to the non-regenerative endothelial cell layer of the cornea;
- it provides a method of heating corneal stroma tissue to correct astigmatism which does not induce irregular astigmatisms;
- it provides a method of heating corneal stroma tissue to correct astigmatism which does not require the passage of electric current through the entire eye, reducing the risk of damage to the cornea, retina, and optic nerve;
- it does not require the use of expensive specialized equipment.

Although the description above contains many specificities, these should not be construed as limiting the scope of the invention, but as merely providing illustrations of some of the presently preferred embodiments of this invention. For example various energy sources such as a cautery probe or a monopolar electrode may be employed to heat stromal tissue in the perilimbal area. Moreover, full correction of an astigmatic cornea may be attained by coagulating tissue at only one pole of the corneal meridian having the lowest keratometric reading and the arcuate segments of coagulated stromal tissue may be varied in length to effect the desired degree of refractive correction.

Thus, the scope of the invention should be determined by the appended claims and their legal equivalents, rather than by the examples given.

I claim:

1. A method of ocular refractive surgery comprising:
  (a) producing with a generator radio frequency energy;
  (b) applying said radio frequency energy produced by said generator to a segment of perilimbal tissue of an eye of a surgical subject by contacting said perilimbal tissue with a transmitting means coupled to said generator; and
  (c) by manipulating said transmitting means, heating and coagulating a corneal stroma layer of said eye underlying said segment of perilimbal tissue, said heating being generated by said applying of said radio frequency energy to said segment of perilimbal tissue of said eye of said surgical subject, whereby a radius of curvature of a central cornea of said eye of said surgical subject is increased.

2. The method of claim 1 wherein said radio frequency energy comprises bipolar radio frequency energy.

3. The method of claim 1 wherein said segment of perilimbal tissue contacts a pole of a corneal meridian of said surgical subject, said corneal meridian having the lowest keratometric reading.

4. The method of claim 1 wherein said segment of perilimbal tissue comprises an arc.

5. The method of claim 4 wherein said arc has a length of between 1 mm to 6 mm.

6. The method of claim 1 wherein said perilimbal tissue comprises a limbus of said eye.

7. The method of claim 1 wherein said perilimbal tissue comprises a clear cornea immediately adjacent to a limbus of said eye.

8. A method of performing ocular refractive surgery comprising:
  (a) producing radio frequency energy with a radio frequency energy source;
  (b) transmitting said radio frequency energy to a segment of perilimbal tissue of an eye of a surgical subject by contacting said segment of perilimbal tissue with an electrode connected to said radio frequency energy source; and
  (c) heating and reorganizing a stroma layer of a cornea beneath said segment of perilimbal tissue by manipulating said electrode, said heating being generated by said transmitting of said radio frequency energy to said segment of perilimbal tissue, whereby a refractive power of a central cornea of said eye of said surgical subject is increased.

9. The method of claim 8 wherein said radio frequency energy comprises bipolar radio frequency energy.

10. The method of claim 8 wherein said segment of perilimbal tissue contacts a pole of a corneal meridian of said surgical subject, said corneal meridian having the lowest refractive power.

11. The method of claim 8 wherein said segment of perilimbal tissue comprises an arcuate segment.

12. The method of claim 11 wherein said arcuate segment has a length of between 1 mm to 6 mm.

13. The method of claim 8 wherein said perilimbal tissue comprises a limbus of said eye.

14. The method of claim 8 wherein said perilimbal tissue comprises a clear cornea immediately adjacent to a limbus of said eye.

* * * * *

UNITED STATES PATENT AND TRADEMARK OFFICE
CERTIFICATE OF CORRECTION

PATENT NO. : 5,423,815
DATED : June 13, 1995
INVENTOR(S) : Richard J. Fugo

It is certified that error appears in the above-identified patent and that said Letters Patent is hereby corrected as shown below:

Abstract
Line 8, change "increase" to -- decrease --

Column 2,
Lines 31, 48, 50, change "increase" to -- decrease --

Column 3,
Line 50, change "increase" to -- decrease --

Column 4,
Line 28, change "increasing" to -- decreasing --
Lines 64, 67-68, change "increases" to -- decreases --

Column 5,
Line 12, change "increase" to -- decrease --

Column 6,
Line 38, change "increased" to -- decreased --

Column 7,
Line 2, change "increased" to -- decreased --

Signed and Sealed this

Fourth Day of September, 2001

*Attest:*

*Attesting Officer*

NICHOLAS P. GODICI
*Acting Director of the United States Patent and Trademark Office*